United States Patent
Deane

(10) Patent No.: US 11,779,417 B2
(45) Date of Patent: Oct. 10, 2023

(54) METHOD OF CONTROLLING A SURGICAL ROBOT

(71) Applicant: CMR SURGICAL LIMITED, Cambridge (GB)

(72) Inventor: Gordon Thomas Deane, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 367 days.

(21) Appl. No.: 17/094,007

(22) Filed: Nov. 10, 2020

(65) Prior Publication Data

US 2021/0137619 A1    May 13, 2021

(30) Foreign Application Priority Data

Nov. 11, 2019  (GB) .................................... 1916402

(51) Int. Cl.
*A61B 1/00*   (2006.01)
*A61B 34/37*   (2016.01)
*A61B 34/30*   (2016.01)

(52) U.S. Cl.
CPC ........ *A61B 34/37* (2016.02); *A61B 2034/301* (2016.02)

(58) Field of Classification Search
CPC ... A61B 2034/301; A61B 34/37; A61B 34/32; A61B 2034/303; A61B 1/00149;
(Continued)

(56) References Cited

U.S. PATENT DOCUMENTS

2002/0111713 A1   8/2002  Wang et al.
2005/0256371 A1  11/2005  Schara et al.
(Continued)

FOREIGN PATENT DOCUMENTS

JP   2011206312 A   10/2011
JP   2019162231 A    9/2019
(Continued)

OTHER PUBLICATIONS

"Law of Cosines", Wikipedia. https://web.archive.org/web/20160329155240/https://en.wikipedia.org/wiki/Law_of_Cosines. Posted/published on Mar. 29, 2016. (Year: 2016).*
(Continued)

*Primary Examiner* — Timothy J Neal
*Assistant Examiner* — James Edward Boice
(74) *Attorney, Agent, or Firm* — Lando & Anastasi, LLP

(57) ABSTRACT

A method of controlling movement of the tip of a surgical endoscope from a first position (E) to an intermediate position (E'), the field of view from the tip of the endoscope being at an angle ($\alpha$) relative to a longitudinal shaft of the endoscope, the method comprising: receiving a command to move from the first position in a first direction; identifying a nominal view point (N) from the tip of the endoscope in the first position; calculating a tip movement path from the first position based on the received command, the identified nominal view point and the angle ($\alpha$); determining the intermediate position; and moving the tip to the intermediate position, the intermediate position being such that the nominal view point remains within the field of view from the tip.

19 Claims, 8 Drawing Sheets

(58) Field of Classification Search
CPC ....... A61B 1/00174; A61B 34/30; A61B 1/00; A61B 90/00; A61B 1/00179; A61B 1/00163–00183
USPC .................. 600/101, 173, 146, 103, 171, 117
See application file for complete search history.

(56) References Cited

U.S. PATENT DOCUMENTS

| | | | | |
|---|---|---|---|---|
| 2012/0053412 | A1* | 3/2012 | Hirakawa | A61B 5/067 600/117 |
| 2014/0378763 | A1* | 12/2014 | Atarot | A61B 34/35 600/109 |
| 2016/0015473 | A1 | 1/2016 | Frimer et al. | |
| 2019/0274524 | A1 | 9/2019 | Nagao | |
| 2019/0350442 | A1* | 11/2019 | Gießen | A61B 1/00179 |
| 2020/0046208 | A1 | 2/2020 | Kasai et al. | |
| 2020/0198147 | A1* | 6/2020 | Fredrickson | B25J 19/027 |
| 2021/0212790 | A1* | 7/2021 | Yoshimura | A61B 90/361 |
| 2022/0168047 | A1* | 6/2022 | Nagao | A61B 1/0016 |
| 2022/0322919 | A1* | 10/2022 | Nagao | A61B 34/30 |

FOREIGN PATENT DOCUMENTS

| | | |
|---|---|---|
| WO | 2018159155 A1 | 9/2018 |
| WO | 2019181149 A1 | 9/2019 |

OTHER PUBLICATIONS

Notification of Transmittal of the International Search Report and the Written Opinion of the International Searching Authority from corresponding PCT/GB2020/052736 dated Feb. 16, 2021.
United Kingdom Search Report from corresponding United Kingdom Application No. GB1916402.9 dated May 4, 2020.
Japanese Notification of Reasons for Refusal from corresponding Japanese Patent Application No. 2022-526775 dated Jun. 6, 2023.

* cited by examiner

METHOD OF CONTROLLING A SURGICAL ROBOT

CROSS-REFERENCE TO RELATED APPLICATION

This application claims the benefit under 35 U.S.C. § 119 of United Kingdom Patent Application No. 1916402.9 filed on Nov. 11, 2019 which is hereby incorporated herein by reference in its entirety for all purposes.

This disclosure relates to controlling the motion of robots, in particular surgical robots and more particularly controlling movement of a surgical endoscope between two positions, typically within a surgical field.

A typical robotic manipulator (or robot) comprises a series of rigid elements which are coupled together by joints. The elements may be joined in series to form an arm. The joints can be driven so as to cause relative motion of the rigid elements. The rigid elements may stem from a base and terminate in an end effector. Thus motion at the joints can be used to position the end effector at a desired location. Each joint may provide rotational motion or linear motion. The joints may be driven by any suitable means, for example electric motors or hydraulic actuators.

When the robot is in operation it will be required to cause the end effector to move to some desired position. For example, the robot may be required to use the end effector to pick up an object. That would require the end effector to be moved to where the object is. To accomplish this, some combination of motions of the joints is required. Calculating those motions is the role of the robot's control system.

FIG. 1 illustrates multiple robots 101, 102, 103 operating in a common workspace. In this example, the robots are surgical robots being used to perform an operation on a person 104. Each robot comprises a base connected to a surgical instrument via a flexible arm. The robots are controlled remotely, in this case by a surgeon. The surgeon is located at a surgeon console 200, shown in FIG. 2. The surgeon manipulates hand controllers 201, 202. A control system converts the movement of the hand controllers into control signals to move the arm joints and/or instrument end effector of a surgical robot. More than one robot may move at the same time.

Endoscopes may have straight or angled optics. Some endoscopes may have an articulated tip which permits both straight and angled configurations. The angled endoscope can be attached to a camera head in different orientations and typically three viewing angles are possible: straight, i.e. along the longitudinal shaft of the endoscope (zero), 30° up or 30° down, with respect to the longitudinal shaft of the endoscope. These example configurations can be seen in FIGS. 7a to 7c. FIG. 7a illustrates a zero° viewing angle, that is a field of view 702 from tip E, such that the mid point 701 of the field of view is at zero° relative to the longitudinal axis of the instrument 404. FIG. 7b shows a 30° up configuration and FIG. 7c shows a 30° down configuration. Whilst 30° is mentioned, as this is the preferred angle, other angles, such as 45° or 60° up or down, are also possible.

In FIGS. 7a to c, a rigid arm member 706 is connected to an attachment 403 by way of a joint 700, which is the example shown is the eight joint of the robot, hence the use of subscript "8". Joint 700 permits attachment 403 to rotate relative to arm member 706 about an axis $z_8$. Attachment 403 has, at the end opposite to joint 700, a surgical instrument 404, in this case an endoscope. The endoscope has at its distal end a viewing tip E. The endoscope tip includes some optics through which the surgeon can see a surgical field once the endoscope has been inserted into a patient. The optics typically pass through the surgical instrument and exit, in this case, via a light pipe 710. The optics may be configured straight, that is with the main viewing axis ($Y_E$) being along or at least parallel to the longitudinal axis of instrument 404, as shown in FIG. 7a. Alternatively, as shown in FIGS. 7b and 7c, the optics may be angled relative to the longitudinal axis of instrument 404. FIG. 7b shows a 30° up arrangement, and FIG. 7c shows a 30° down configuration.

Often a surgeon will need to alter the position of a tip of the endoscope so as to zoom in or zoom out of the surgical field so as to obtain an appropriately scaled image of the surgical field. This requires a change in the depth of the endoscope tip within the surgical field.

The endoscope attached to the surgical robot passes into the patient being operated on through an opening, typically a small opening with limited or no side to side movement of the endoscope being permitted. This opening therefore defines a virtual pivot point (VPP) through which the endoscope must pass. In an alternative, a physical pivot point may be created, for example by way of a structural element through which the endoscope passes, or a pivot point may be defined by the locking of one or more joints on the robot arm. In this way, a mechanical pivot point is created. Any reference to "virtual pivot point", "mechanical pivot point" or "pivot point" is intended to cover all options for the creation of pivot point unless expressly stated otherwise. The endoscope will have a nominal view point (N) located at a distance n from the endoscope tip. n may be estimated as the expected distance from the endoscope tip to the surgical field that the surgeon wishes to view.

When using a straight endoscope, i.e. one in which the line of sight from the camera is along, or at least parallel to, the endoscope shaft, such a change in depth is relatively straightforward. When the surgeon commands a change in depth of the endoscope tip, a control unit associated with the surgical robot calculates the necessary robot arm movements.

For an angled endoscope (i.e. having a non-zero viewing angle), the motion problem is more complex. There is no simple way to move exactly into or out of the subjective view, i.e. towards or away from the nominal view point, because any motion of the tip inherently causes the view to tilt and therefore the direction of "into the view" changes. Merely moving an angled endoscope along the shaft line of the endoscope makes it difficult to move in and out of the workspace because the pitch control of the tip of the endoscope has to be used to compensate for the line of motion.

Thus, it would be beneficial to provide an improved method of controlling a surgical endoscope.

According to the present invention, there is provided a method of controlling movement of the tip of a surgical endoscope from a first position (E) to an intermediate position (E'), the field of view from the tip of the endoscope being at an angle (α) relative to a longitudinal shaft of the endoscope, the method comprising: receiving a command to move from the first position in a first direction; identifying a nominal view point (N) from the tip of the endoscope in the first position; calculating a tip movement path from the first position based on the received command, the identified nominal view point and the angle (α); determining the intermediate position; and moving the tip to the intermediate position, the intermediate position being such that the nominal view point remains within the field of view from the tip.

The calculating step may include calculating a curved path for the tip movement path. The curved path may be elliptical. The curved path may be a circle passing through a pivot point (V), the first position (E) and the nominal view point (N).

The calculating step may include calculating a tangent to the curved path at E. The tangent may lie in a plane containing V, E and N. The intermediate position may be along the tangent.

Movement of the tip may be along the tip movement path. Movement of the tip to the intermediate position may be along the tangent.

Once the tip is in the intermediate position, the method may further comprise (i) recalculating the tip movement path from the intermediate position, (ii) determining a new intermediate position and (iii) moving the tip to the new intermediate position.

Steps (i) to (iii) may be repeated one or more times. Steps (i) to (iii) may be repeated until the intermediate position becomes the final position.

The frequency of the repeated calculations may be between 500 Hz and 10 kHz, preferably at 5 kHz.

The nominal view point (N) may be at a distance (n) from the tip, wherein n is fixed.

The nominal view point (N) may be at a distance (n) from the tip, wherein n is variable.

The first direction may include a component of motion that changes n.

The command may include a command to zoom in towards the nominal view point.

The command may include a command to zoom out away from the nominal view point.

The nominal view point may not alter, i.e. it is fixed in three dimensional space by one or more determining factors.

The angle ($\alpha$) may be plus or minus 30, 45 or 60 degrees relative to the longitudinal shaft of the endoscope.

During the moving step, the endoscope may move axially through a pivot point through which the endoscope must pass.

The first direction may comprise one or more components of motion from the following: motion in the x axis; motion in the y axis; motion in the z axis; pitch; roll; or yaw.

The step of calculating the intermediate position may include determining the centre $O_w$ of the circle using the following:

$$O_W = V_W + \begin{bmatrix} \pm\sqrt{r^2 - \left(\frac{d}{2}\right)^2} \\ 0 \\ d/2 \end{bmatrix}$$

where r is the radius of the circumcircle of triangle (V, E, N) and d is the depth of the endoscope within the patient.

The radius (r) may be determined using the depth (d) of the endoscope from the V and the predetermined distanced (n) using the following:

$$r = \sqrt{d^2 + n^2 + dn\sqrt{3}}$$

The invention also provides a surgical robot having a controllable arm on which a surgical endoscope can be mounted and a control unit configured to carry out a method as described above.

BRIEF DESCRIPTION OF THE FIGURES

The present disclosure will now be described by way of example with reference to the accompanying drawings. In the drawings.

DETAILED DESCRIPTION

The following description relates to a robotic system comprising a plurality of robots and a control unit. The control unit drives the robots to move. Position and torque sensors on the robot arms relay sensory data to the control unit. The control unit uses this sensory data to detect external forces acting on the robot arms.

Figure 3:
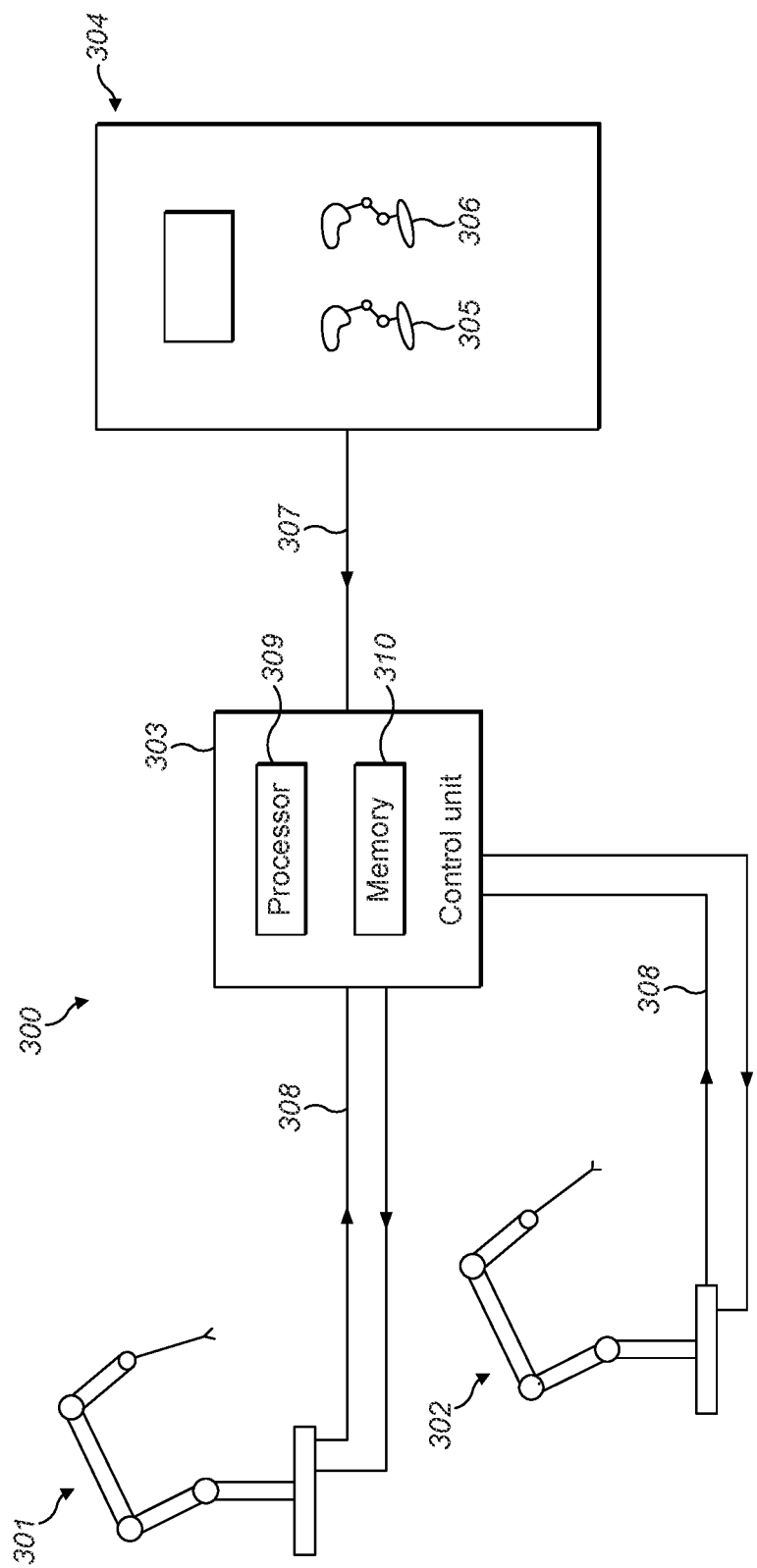
FIG. 3 illustrates a schematic diagram of a robotic system.

The following examples relate to a surgical robotic system. With reference to FIG. 3, the surgical robotic system 300 comprises two surgical robots 301, 302 driven by a control unit 303. The control unit 303 receives one or more inputs 307 from a surgeon's console 304, including inputs from first and second hand controllers 305, 306. The inputs typically correspond to one or more motion control commands relating to movement of one or more of the arms (see 402 in FIG. 4) of the of the surgical robots. The control unit may receive other inputs 307 from the surgeon's console, such as foot pedal(s) inputs, button inputs, voice recognition inputs, gesture recognition inputs, eye recognition inputs etc. The control unit 303 also receives inputs 308 from the surgical robots 301, 302. These inputs include sensory data from position sensors and torque sensors located on the robot arm joints. The control unit 303 may receive other inputs 308 from each robot, such as force feedback, data from the surgical instrument etc. The control unit 303 drives the robots 301, 302 in response to the inputs it receives from the robots and the surgeon's console. The control unit 303 comprises a processor 309 and a memory 310. The memory stores, in a non-transient way, software code that can be executed by the processor to cause the processor to control the drivers in the manner described herein.

Figure 4:
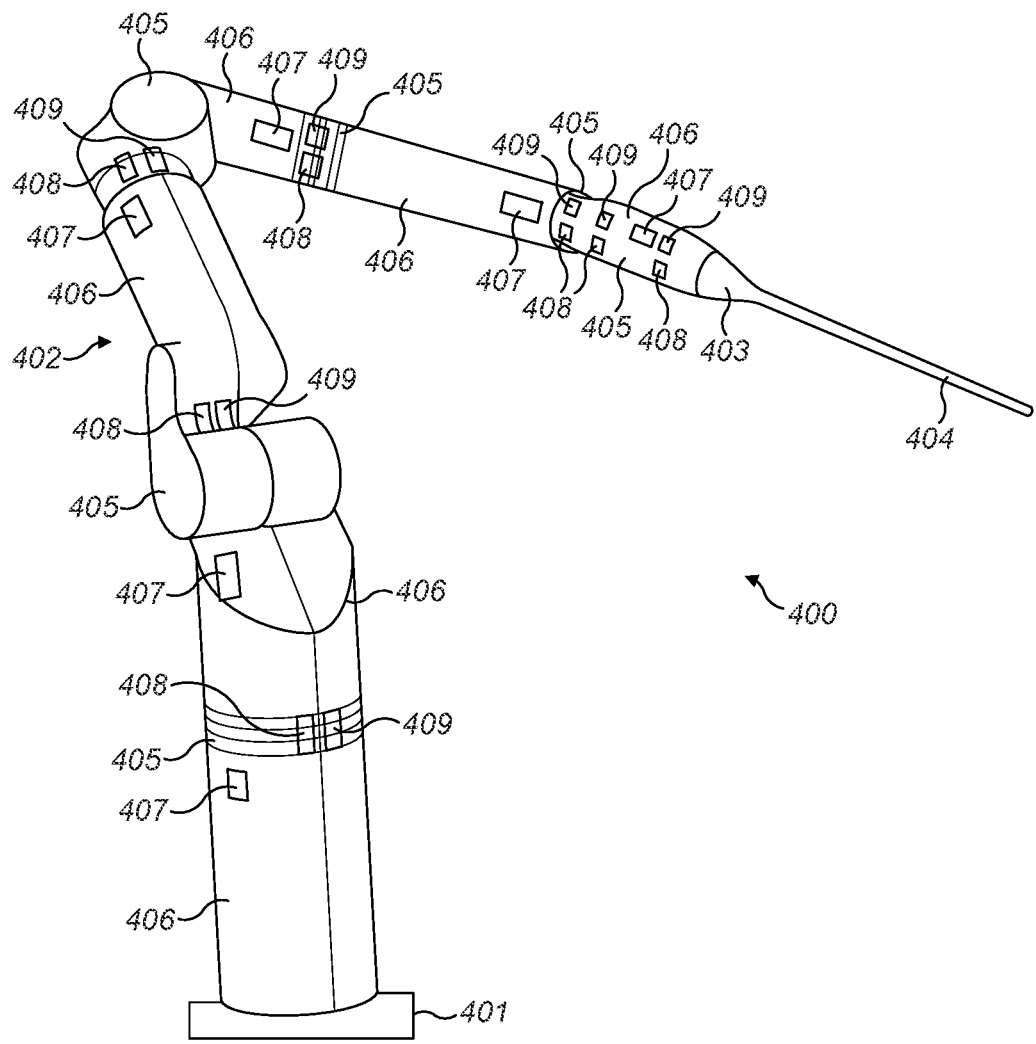
FIG. 4 illustrates a robot.

Each robot 301, 302 is of the form 400 illustrated in FIG. 4. The robot comprises a base 401 which is fixed in place when a surgical procedure is being performed. Suitably, the base 401 is mounted to a chassis. That chassis may be a cart, for example a bedside cart for mounting the robot at bed height. Alternatively, the chassis may be a ceiling mounted device, or a bed mounted device.

An arm 402 extends from the base 401 of the robot to an attachment 403 for a surgical instrument 404. The arm is flexible. It is articulated by means of multiple flexible joints 405 along its length. In between the joints are rigid arm members 406. The arm in FIG. 4 has seven joints. The joints include one or more roll joints (which have an axis of rotation along the longitudinal direction of the arm members on either side of the joint), one or more pitch joints (which have an axis of rotation transverse to the longitudinal direction of the preceding arm member), and one or more yaw joints (which also have an axis of rotation transverse to the longitudinal direction of the preceding arm member and also transverse to the rotation axis of a co-located pitch joint). However, the arm could be jointed differently. For example, the arm may have fewer or more joints. The arm may include joints that permit motion other than rotation between respective sides of the joint, for example a telescopic joint. The robot comprises a set of drivers 407, each driver 407 drives one or more of the joints 405.

The attachment 403 enables the surgical instrument 404 to be releasably attached to the distal end of the arm. The surgical instrument 404 has a linear rigid shaft and a working tip at the distal end of the shaft. The working tip comprises an end effector for engaging in a medical procedure. The surgical instrument may be configured to extend linearly parallel with the rotation axis of the terminal joint of the arm. For example, the surgical instrument may extend along an axis coincident with the rotation axis of the terminal joint of the arm. The surgical instrument 404 could be, for example, a cutting, grasping, cauterising or imaging device.

The robot arm comprises a series of sensors 408, 409. These sensors comprise, for each joint, a position sensor 408 for sensing the position of the joint, and a torque sensor 409 for sensing the applied torque about the joint's rotation axis. One or both of the position and torque sensors for a joint may be integrated with the motor for that joint. The outputs of the sensors are passed to the control unit 303 where they form inputs for the processor 309.

Figure 6A:
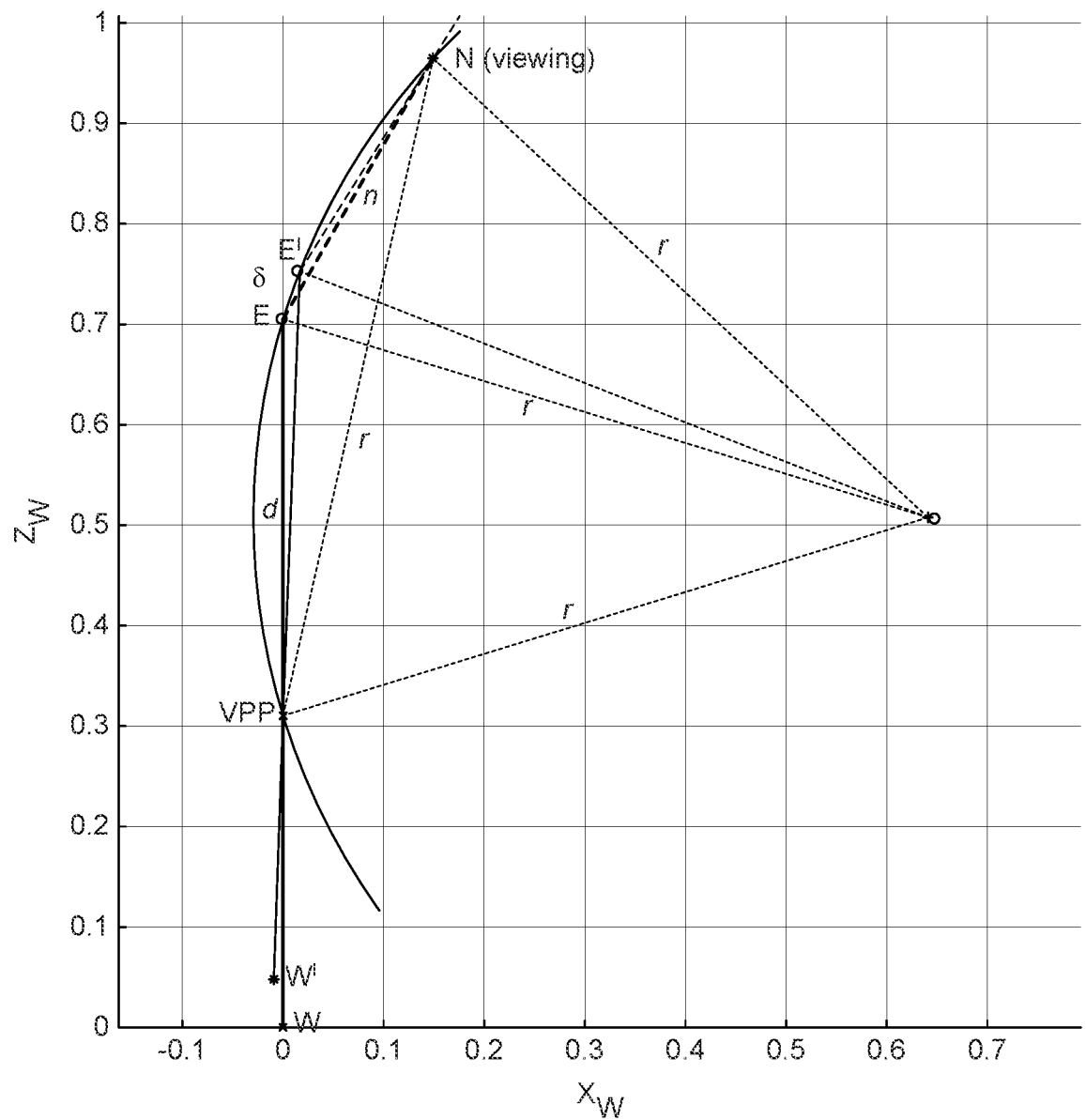
FIGS. 6a and 6b are schematic representations of the movement into (FIG. 6a) and out of (FIG. 6b) a surgical field.
Figure 6B:
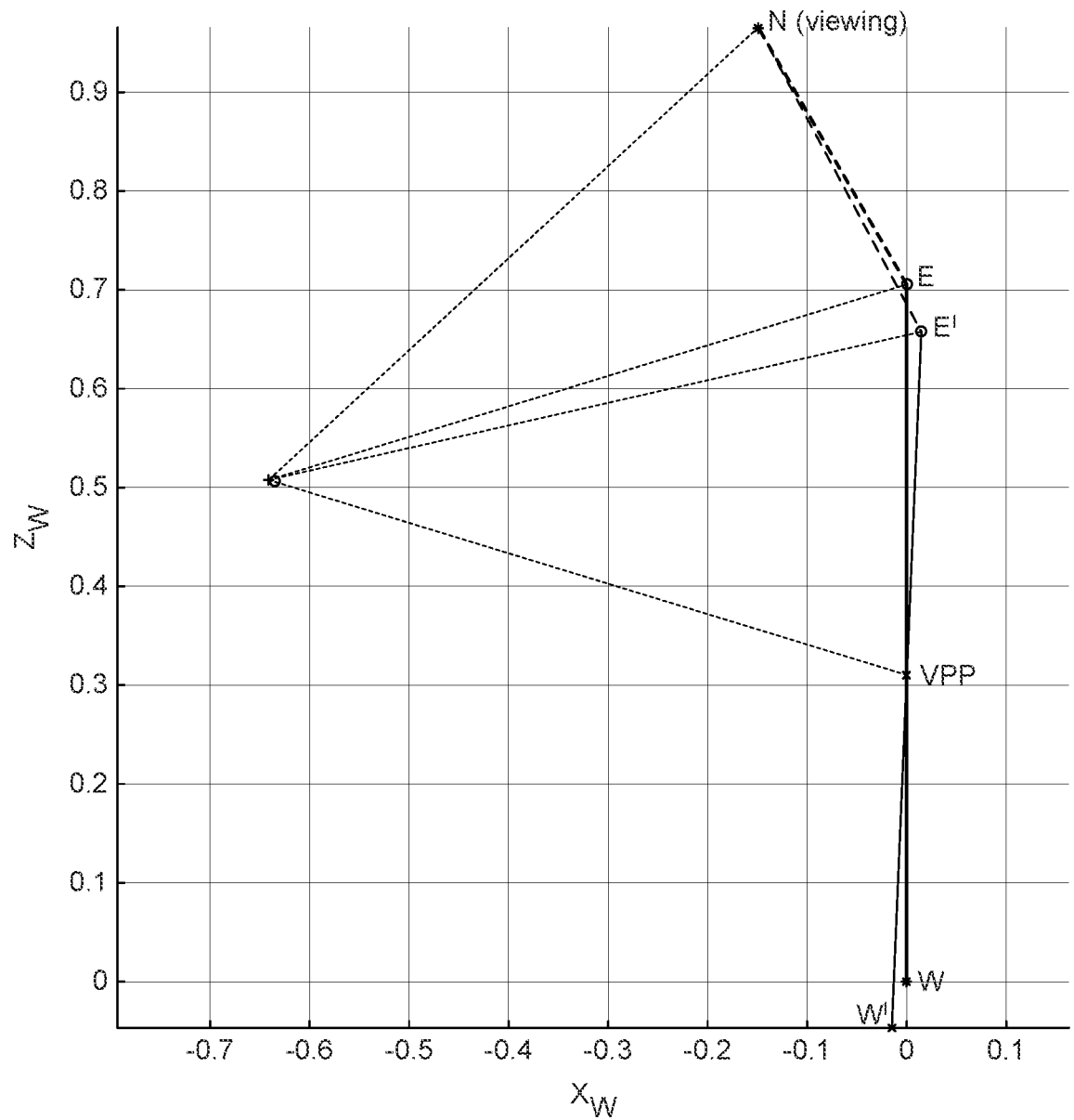

FIG. 6a illustrates inward motion geometry, with an angled endoscope attached in a 30° down orientation. The following discussion assumes the 30° down orientation, but would be equally applicable to other angle configurations with appropriate changes to the angles within the calculations. This inward motion is required when a surgeon wishes to zoom in on the nominal view point. In contrast, FIG. 6b illustrates outward motion geometry, with an angled Endoscope attached as 30° up. This outward motion is required when a surgeon wishes to zoom out from the nominal view point.

Figure 1:
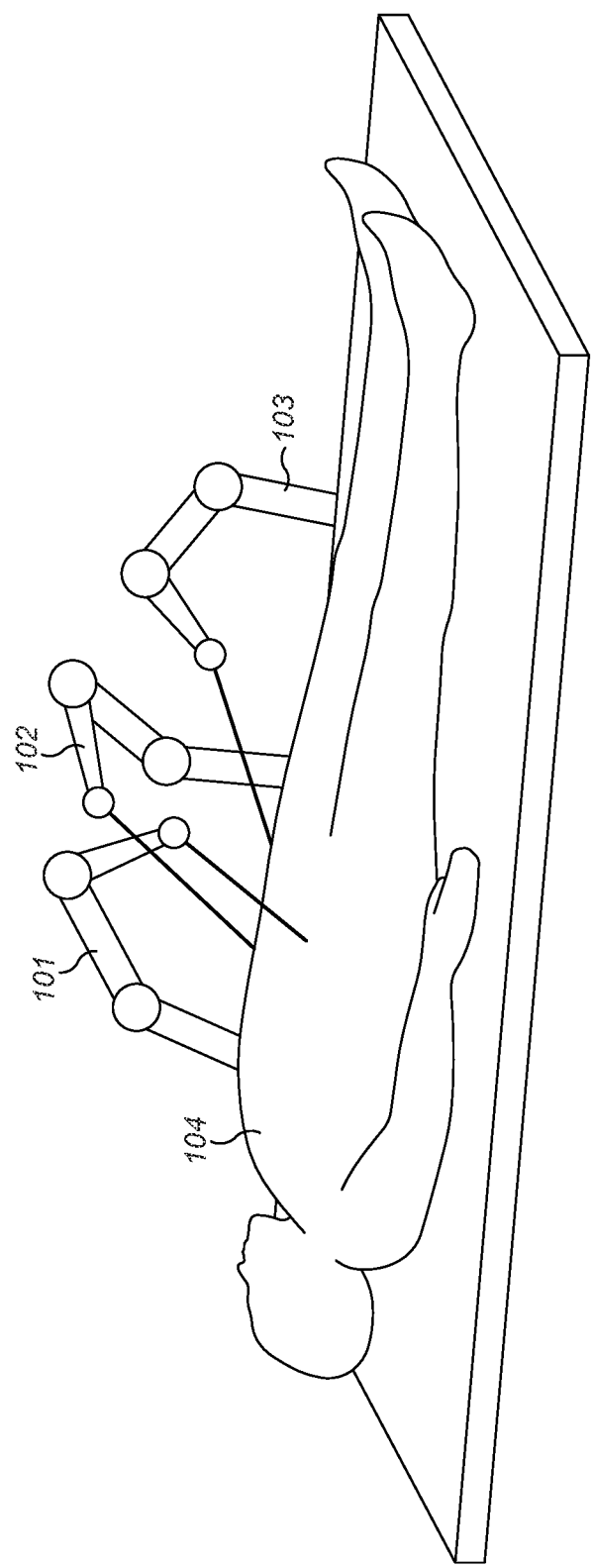
FIG. 1 illustrates a person being operated on by a robotic system comprising three surgical robots.
Figure 2:
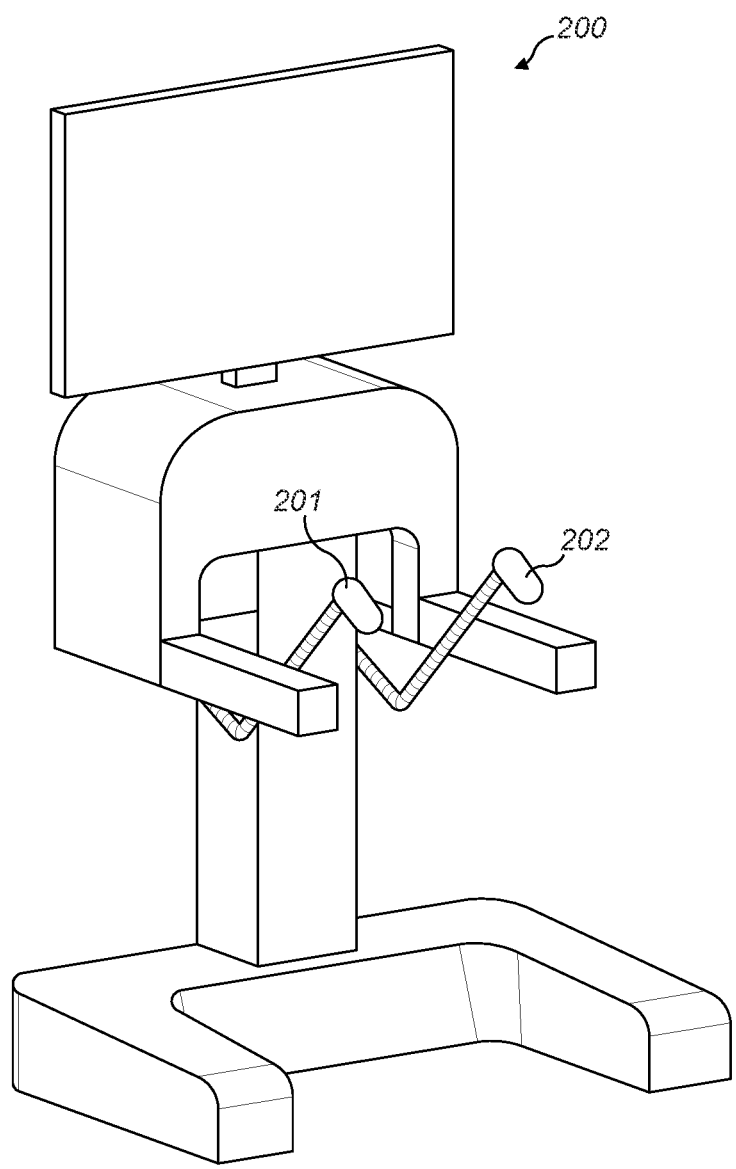
FIG. 2 illustrates a surgeon's console.

The approach adopted by the present invention uses a nominal viewing point N, the view angle of the tip of the endoscope relative to the endoscope shaft and any control commands to determine the most appropriate movement path for the endoscope tip. The nominal view point may be a fixed position in three dimensional space, or may, as is described in this example, be at a fixed distance, or "viewing distance parameter," n along $y_E$ ("i.e. into the screen" of the console shown in FIG. 2). This is shown in FIG. 6a and FIG. 6b where the endoscope tip position is E, the viewing line is EN and the distance |E-N| is the viewing distance parameter n which is a distance in the XZ plane in FIG. 6a.

Whilst n is a fixed distance in this example, it may be a variable for example in dependence on another parameter such as depth of the endoscope tip within the patient, i.e. distance from the pivot point, or perhaps N might be a fixed position (for example determined by a surgeon as a fixed position in the surgical field), such that n must inherently vary as the endoscope tip moves.

The objective is to find a new Endoscope Shaft tip position E' (and a new wrist position W' preserving the VPP) such that |E-E'|=δ and that the new line of view from E' also goes through N. So for small δ, an object at N would remain in the centre of the view on the surgeon's display. In this example, the calculation requires the determination of a circular path as described in the following. In an alternative, a different curved path, for example following an elliptical path or a different complex path such as algebraic curves, transcendental curves, piecewise constructions or any combination of these.

Key in FIGS. 6a and 6b:
W—prior Wrist origin
E—Endoscope tip
W', E'—updated points after a timestep. Timestep distance is exaggerated for illustration.
N—nominal viewing point $E+n*y_E$
VPP—Virtual Pivot Point (although may be a mechanical pivot point instead)
O—centre of circumcircle of triangle (VPP, E, N)
r—radius of circumcircle of triangle (VPP, E, N)
d=|VPP-E|='depth' of insertion of the endoscope within the patient
δ=commanded depth change (typically 10E-7 m to 10E-4 m for the sampling frequency disclosed herein)

The angle VPP-E-N=VPP-E'-N=150° because these are the viewing lines of the optics. So E' is on the circumcircle of VPP-E-P with centre at O, that is, let $$r=|O-VPP|=|O-E|=O-E'|=|O-N|$$

The angle VPP–O–N is 60°; this is twice the angle subtended by VPP–N on the far side of the circle, which is 180°–150°=30° (from the cyclic quadrilateral theorem, i.e. the opposite angles of a cyclic quadrilateral are supplementary). So VPP–O–N is an equilateral triangle with side r.

We now find E' by first finding O in terms of d, n and VPP.
The coordinates of O in the frame W are given (from the geometry of W, VPP, O and E) by:

$$O_W = VPP_W + \begin{bmatrix} \pm\sqrt{r^2-\left(\frac{d}{2}\right)^2} \\ 0 \\ d/2 \end{bmatrix}$$

The sign ± depends on whether the endoscope is fitted as 30° down (+) or 30° up (−). The latter case is shown in FIG. 6b, which also illustrates the case of outward motion where δ<0.

To find r terms of d and n, we can use the cosine rule on triangle VPP–E–N, $$r^2 = d^2 + n^2 - 2\,dn\cos 150°$$

$$\therefore r = \sqrt{d^2+n^2+dn\sqrt{3}}$$

Now the intention is for |E-E'| to be the commanded depth change δ, so in principle E' is the point on the circle centred as O but with a chord length of δ towards N.

Because the position update is done at a high rate (e.g. between 500 Hz to 10 kHz, preferably at 5 kHz), the individual timesteps are typically very small, and EE' may then be approximately the tangent to the circle at E. Therefore it may be possible to use a simpler approximation that computes the tangent rather than the chord. Given that the distance from E to E' is very small, E' is typically an intermediate position. At some stage, E' will become the final position that the surgeon wishes to reach.

Taking the unit vector along the radius OE:

$$\vec{OE_W} = \frac{E_W - O_W}{|E_W - O_W|}$$

Figure 7A:
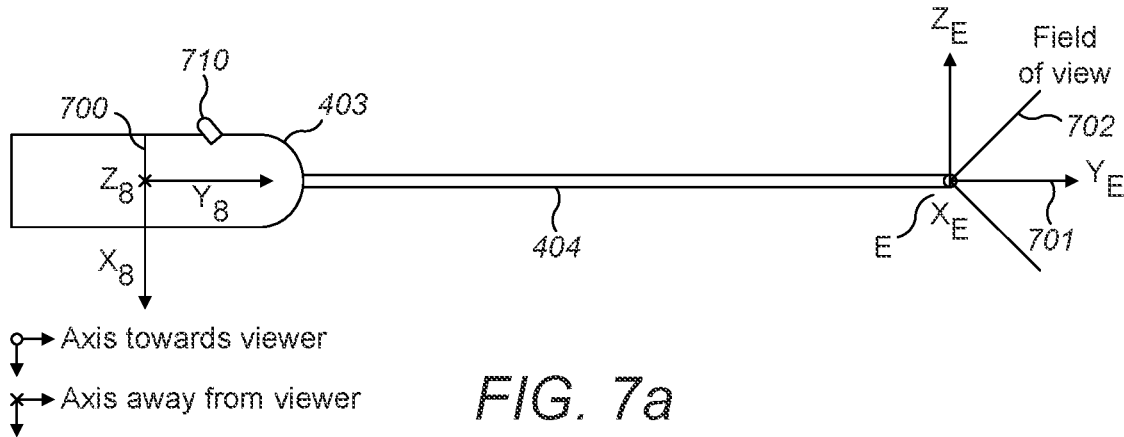
FIGS. 7a to c show different viewing configurations of endoscope tips.
Figure 7B:
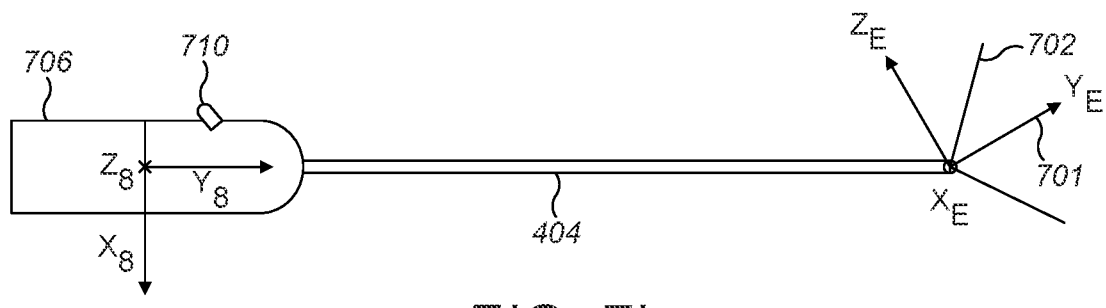
Figure 7C:
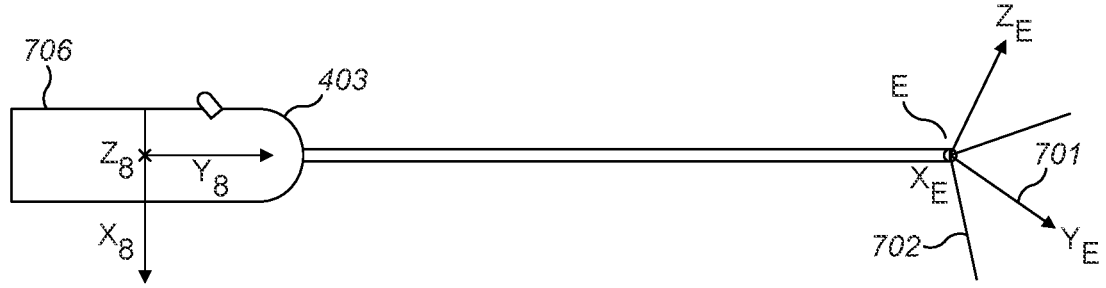

Then rotate this by $\pi/2$ about the axis perpendicular to the axis of rotation of joint 700 (see FIGS. 7a to c)—this axis can be referred to as γ8—in the 30° down or $-\pi/2$ in the 30° up case; the ± is the same as for the square root above. The z8 axis may be coincident with, i.e. the same as, the end effector shaft axis 404, or may be parallel to that axis. When coincident, the z8 axis is also the same as the view axis ($\gamma_E$) for straight endoscopes. The γ8 axis is perpendicular to the z8 axis, and according to FIG. 6a "into the page" at E.

$$\vec{EE'_W} = \begin{bmatrix} 0 & 0 & \mp 1 \\ 0 & 1 & 0 \\ \pm 1 & 0 & 0 \end{bmatrix} \vec{OE_W}$$

$$E' = E + \delta \cdot \vec{EE'_W}$$

The Endoscope Arm Wrist pose, i.e. the position and orientation of the endoscope, can then be calculated from E' and the VPP.

Once the tip has moved to E', E' becomes the new E and the system may recalculate a new E' based around the new starting position E. The recalculation may continue until E' is the final position in which the surgeon wishes the tip to be placed in which case no further recalculation is required. This recalculation is typically required when E' does not lie on the calculated path, but rather is along a tangent from E, as described above. In this situation, the actual movement of the tip does not follow the calculated path. The tip may trace a path which is circular, elliptical or a more complex curve such as a spiral. The traced path may be the same as the calculated path, but may be different. The path traced by the tip may be a series of straight line movements, which due to their shortness (see δ above) may approximate a curve.

In an alternative, once the path is calculated, it may be possible for the movement of the tip to be controlled such that it follows the calculated path, in which case recalculation may not be required.

The viewing distance parameter is preferably tuned as, in the 30° case, although this viewing distance parameter n has no 'perfect' value. In the limit where n→0, the radius r→d and the tangent EE' becomes the same as the viewing line EN. This corresponds to moving in or out along the normal of the telescope optics. While this is theoretically appealing it tends to "pitch down" as you move in and does not maintain the illusion of moving "straight in" as effectively as a larger n value.

In the limit where n→∞, the tangent EE' becomes the endoscope axis and this method reduces to moving along the endoscope axis, which we are generally avoiding for angled, such as 30°, endoscopes as described above.

The value has been tuned empirically and n=0.1 metres has been identified as the most appropriate value. It may be possible to have value for n that can be varied, either in dependence upon a fixed variable such as tip angle (i.e. n is different for different tip angles), or in dependence upon a more continuous variable such as the changing depth of the endoscope within the body, i.e. as depth changes, n changes in some relationship to depth.

If the tip is very close to the pivot point, on either side, then this 30° motion model could cause undesirably high velocities in one or more joints of the robot arm. Additionally the vision tends to be of the port itself, so moving at an imaginary object in view is less useful. Therefore when the depth is less than a threshold value, the control unit may revert to motion along the shaft line (i.e. n→∞) as in the straight endoscope case.

Figure 5:
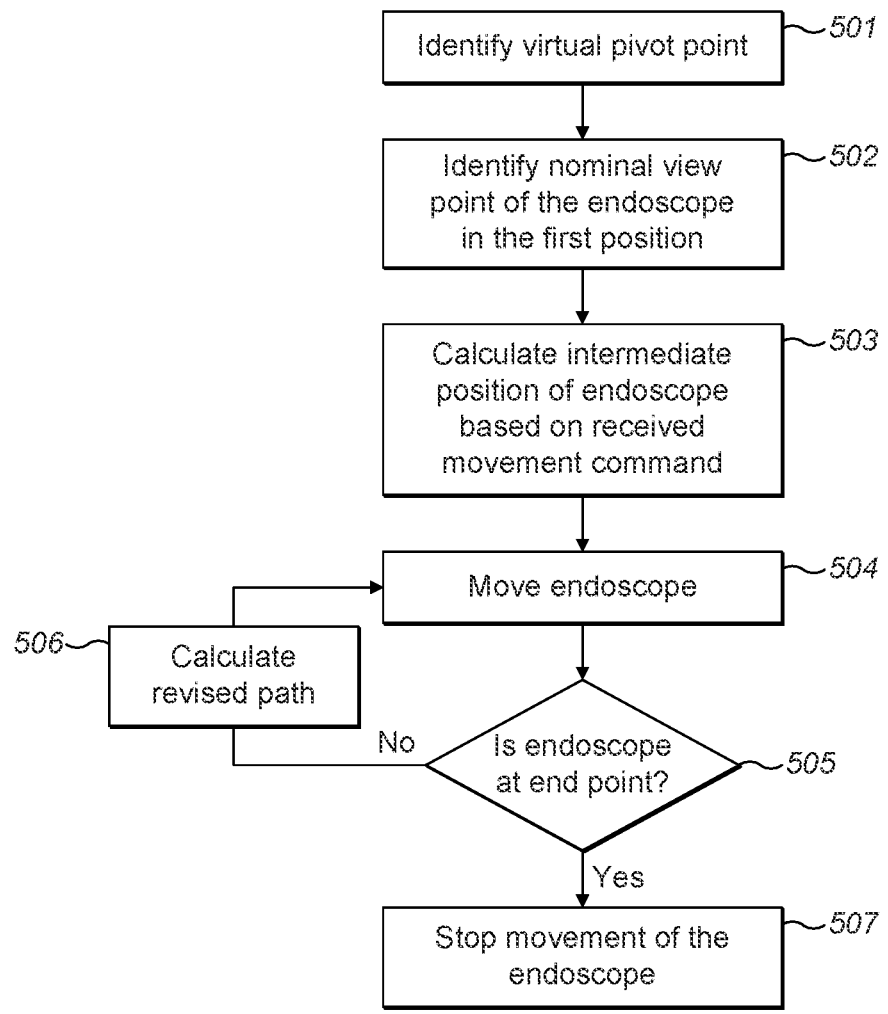
FIG. 5 is a flowchart showing the process of moving an endoscope tip from a first position to a second position.

FIG. 5 is a flow chart showing the simplest form of the method of the invention. Once a suitable opening for insertion of the surgical endoscope has been created in the patient including the fitting of any suitable port or other item through which the endoscope will pass, this opening defines the virtual pivot point (step 501). The location within the patient at which the surgeon operates is identified and the endoscope positioned, typically at viewing distance parameter n, such that the nominal view point is identified (step 502) at the predetermined distance n from the tip of the endoscope in the first position. The nominal view point may however be identified prior to identifying the VPP, for example if the system sets a desired view point for example after imaging the patient being operated upon to identify a location of interest. The system then, at step 503, receives a command to move the endoscope, due to one or more motion inputs typically from the surgeon, and then calculates an intermediate position E' for the tip of the endoscope on a circular path passing through the virtual pivot point, the nominal view point and the first position E, in line with the example given above. This intermediate position is dependent upon the input from the surgeon concerning whether it is a zooming in or zooming out that is required, and the extent of that zoom. At step 504, the tip of the endoscope is moved towards the intermediate position, the intermediate position being such that the nominal view point would be within the view from the tip. The word "towards" does not mean in a direct line towards the second position, but encompasses any motion that reduces the distance between the endoscope tip position E and the nominal view point N. As described above, this motion may be along the circular path that has been calculated, or may take the form of one or more tangential steps, the steps being tangential to the circular path. The method may also include, possibly after a relatively small movement of the tip or after a given time duration, the calculation of a revised or alternative circular path, as at step 506. This may also include a decision (step 505) about whether or not the tip has reached the desired final position, i.e. the position to which the surgeon wishes to move. The reason for the further calculation would be that if or when N changes, and/or the depth of the tip within the patient alters, the circular path that was originally calculated is no longer correct for the new position E' of the endoscope tip and/or the other variable factors such as the new position of N. As such, a new "r" is calculated defining a new circular path, meaning that the endoscope tip moves "towards" the nominal view point either along the new path or in a series of one or more tangential steps. This updating of the calculation may be done at a frequency of between 500 hz to 10 kHz or after the endoscope tip has moved a certain distance, either a linear distance or an arcuate distance. Thus, the actual path followed by the endoscope tip may be circular, in line with the initial calculation of the intermediate position, or may follow an ellipse or other geometric shape. Once the tip has reached the desired position, i.e. E' is the desired position, movement stops (step 507). The desired position is typically determined only once the surgeon has released the controls, i.e. is providing no more inputs affecting movement of the endoscope.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A method of controlling movement of the tip of a surgical endoscope from a first position (E) to an intermediate position (E'), the field of view from the tip of the endoscope being at an angle (a) relative to a longitudinal shaft of the endoscope, the method comprising:
   receiving a command to move from the first position in a first direction;
   identifying a nominal view point (N) from the tip of the endoscope in the first position;
   calculating a curved tip movement path from the first position based on the received command, the identified nominal view point and the angle (a);
   determining the intermediate position; and
   moving the tip to the intermediate position, the intermediate position being such that the nominal view point remains within the field of view from the tip,
   wherein the curved tip movement path is either elliptical or a circle passing through a pivot point (V), the first position (E) and the nominal view point (N).

2. A method according to claim 1, wherein the calculating step includes calculating a tangent to the curved path at E.

3. A method according to claim 2, wherein the tangent lies in a plane containing V, E and N.

4. A method according to claim 2, wherein the intermediate position is along the tangent.

5. A method according to claim 1, wherein movement of the tip is along the tip movement path.

6. A method according to claim 2, wherein the movement of the tip to the intermediate position is along the tangent.

7. A method according to claim 1, wherein, once the tip is in the intermediate position, the method further comprises (i) recalculating the tip movement path from the intermediate position, (ii) determining a new intermediate position and (iii) moving the tip to the new intermediate position.

8. A method according to claim 7, wherein steps (i) to (iii) are repeated until the intermediate position becomes the final position.

9. A method according to claim 1, wherein the nominal view point (N) is at a distance (n) from the tip, wherein n is fixed.

10. A method according to claim 1, wherein the nominal view point (N) is at a distance (n) from the tip, wherein n is variable.

11. A method according to claim 10, wherein the first direction includes a component of motion that changes n.

12. A method according to claim 1, wherein the command includes a command to either zoom in towards the nominal view point or zoom out away from the nominal view point.

13. A method according to claim 1, wherein the nominal view point does not alter.

14. A method according to claim 1, wherein the angle (a) is plus or minus 30, 45 or 60 degrees relative to the longitudinal shaft of the endoscope.

15. A method according to claim 1, wherein, during the moving step, the endoscope moves axially through a pivot point through which the endoscope must pass.

16. A method according to claim 1, wherein the first direction comprises one or more components of motion from the following: motion in the x axis; motion in the y axis; motion in the z axis; pitch; roll; or yaw.

17. A method according to claim 1, wherein the step of calculating the intermediate position includes determining the centre O of the circle using the following:

$$O_W = V_W + \begin{bmatrix} \pm\sqrt{r^2 - \left(\frac{d}{2}\right)^2} \\ 0 \\ d/2 \end{bmatrix}$$

where r is the radius of the circumcircle of triangle (V, E, N) and d is the depth of the endoscope within the patient.

18. A method according to claim 1, wherein the radius (r) is determined using the depth (d) of the endoscope from the V and the predetermined distanced (n) using the following:

$$r = \sqrt{d^2 + n^2 + dn\sqrt{3}}$$

19. A surgical robot having a controllable arm on which a surgical endoscope can be mounted and a control unit configured to carry out a method of controlling movement of the tip of a surgical endoscope from a first position (E) to an intermediate position (E'), the field of view from the tip of the endoscope being at an angle (a) relative to a longitudinal shaft of the endoscope, the method comprising:
   receiving a command to move from the first position in a first direction;
   identifying a nominal view point (N) from the tip of the endoscope in the first position;
   calculating a curved tip movement path from the first position based on the received command, the identified nominal view point and the angle (a);
   determining the intermediate position; and
   moving the tip to the intermediate position, the intermediate position being such that the nominal view point remains within the field of view from the tip,
   wherein the curved tip movement path is either elliptical or a circle passing through a pivot point (V), the first position (E) and the nominal view point (N).

* * * * *